(12) United States Patent
Sakai

(10) Patent No.: US 12,740,764 B2
(45) Date of Patent: Sep. 22, 2026

(54) ULTRASOUND DIAGNOSTIC APPARATUS, ULTRASOUND DIAGNOSTIC METHOD, AND RECORDING MEDIUM

(71) Applicant: Konica Minolta, Inc., Tokyo (JP)

(72) Inventor: Takashi Sakai, Yokohama (JP)

(73) Assignee: Konica Minolta, Inc., Tokyo (JP)

( * ) Notice: Subject to any disclaimer, the term of this patent is extended or adjusted under 35 U.S.C. 154(b) by 0 days.

(21) Appl. No.: 18/954,678

(22) Filed: Nov. 21, 2024

(65) Prior Publication Data

US 2025/0169794 A1 May 29, 2025

(30) Foreign Application Priority Data

Nov. 28, 2023 (JP) ................................ 2023-200469

(51) Int. Cl.
*A61B 8/00* (2006.01)

(52) U.S. Cl.
CPC .................................. *A61B 8/461* (2013.01)

(58) Field of Classification Search
CPC .......... A61B 8/461; A61B 8/465; A61B 8/463
See application file for complete search history.

(56) References Cited

U.S. PATENT DOCUMENTS

2014/0221835 A1* 8/2014 Ota ........................ A61B 8/463 600/443
2025/0173943 A1* 5/2025 Dai ........................ G06T 13/40

FOREIGN PATENT DOCUMENTS

JP H02237555 A 9/1990

* cited by examiner

*Primary Examiner* — Alexei Bykhovski
(74) *Attorney, Agent, or Firm* — RANKIN, HILL & CLARK LLP

(57) ABSTRACT

Disclosed is an ultrasound diagnostic apparatus, including: a generator that irradiates a subject with an ultrasound wave to generate ultrasound image data based on the ultrasound wave reflected off the subject; and a hardware processor that displays an ultrasound image based on the ultrasound image data on a screen of a display part. In a display mode in which the screen is divided into a plurality of display areas, the hardware processor: displays an ultrasound image of a predetermined examination part and identification information for specifying the examination part of the ultrasound image in each display area; and, in response to a change made in a position and/or a size of the identification information in one display area among the plurality of display areas, executes conjunction control of changing the position and/or the size of the identification information in another display area in conjunction with the change.

8 Claims, 9 Drawing Sheets

20
200
220
COMMUNICATOR
214
DISPLAY PART
212
DISPLAY CONTROLLER
240
STORAGE
241
PROGRAM
230
CONTROLLER
210
IMAGE PROCESSOR
211
IMAGE MEMORY
202
OPERATION PART
208
IMAGE GENERATOR
204
TRANSMITTER
206
RECEIVER
250
254
256
252
ULTRASOUND PROBE
253

| FETUS | ABDOMEN | RIGHT BREAST | LEFT BREAST | SHOULDER | ··· |
|---|---|---|---|---|---|
|  |  | R | L | R | ··· |

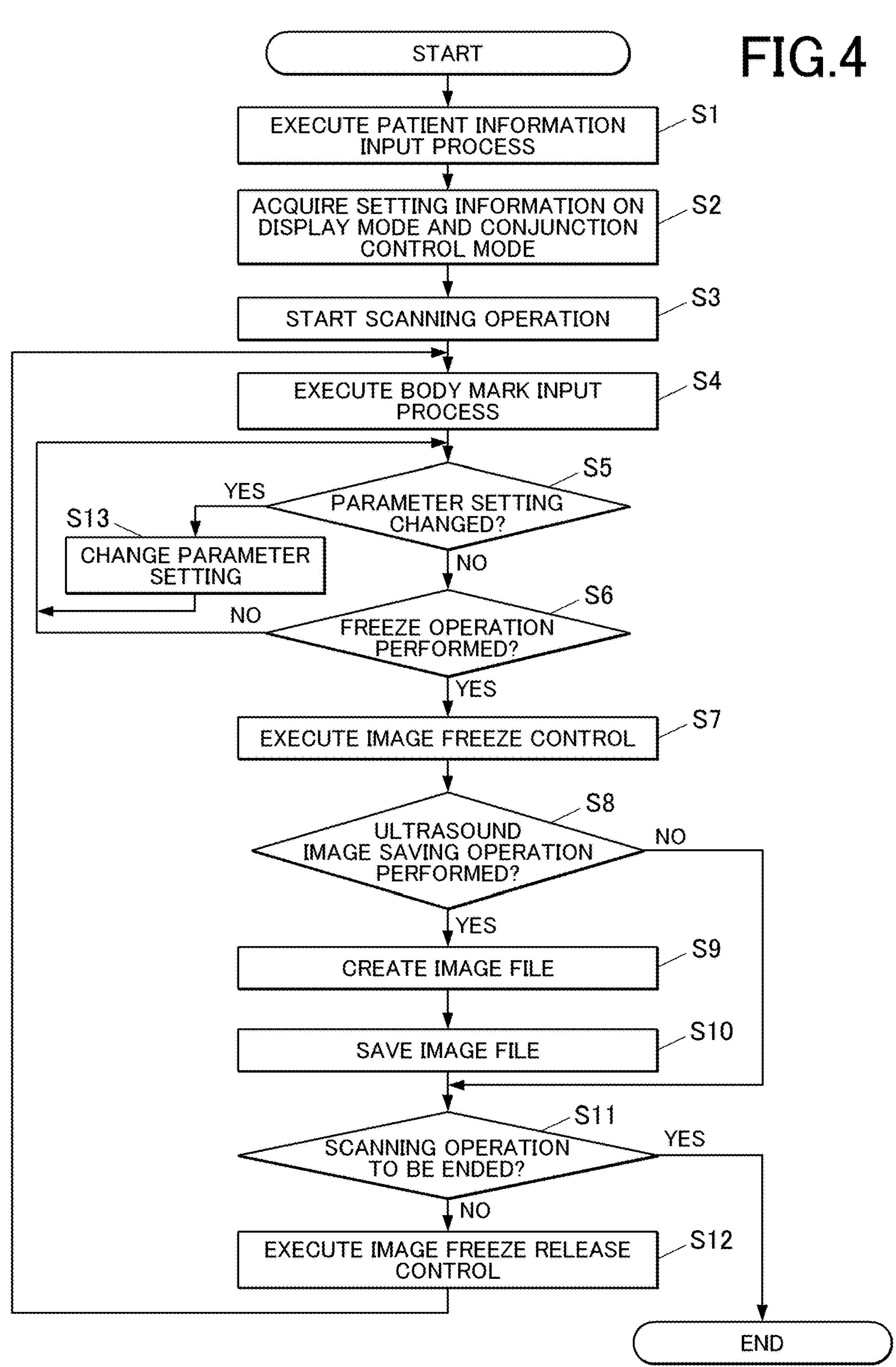
FIG.4
START
EXECUTE PATIENT INFORMATION INPUT PROCESS
S1
ACQUIRE SETTING INFORMATION ON DISPLAY MODE AND CONJUNCTION CONTROL MODE
S2
START SCANNING OPERATION
S3
EXECUTE BODY MARK INPUT PROCESS
S4
PARAMETER SETTING CHANGED?
S5
YES
S13
CHANGE PARAMETER SETTING
NO
FREEZE OPERATION PERFORMED?
S6
NO
YES
EXECUTE IMAGE FREEZE CONTROL
S7
ULTRASOUND IMAGE SAVING OPERATION PERFORMED?
S8
NO
YES
CREATE IMAGE FILE
S9
SAVE IMAGE FILE
S10
SCANNING OPERATION TO BE ENDED?
S11
YES
NO
EXECUTE IMAGE FREEZE RELEASE CONTROL
S12
END

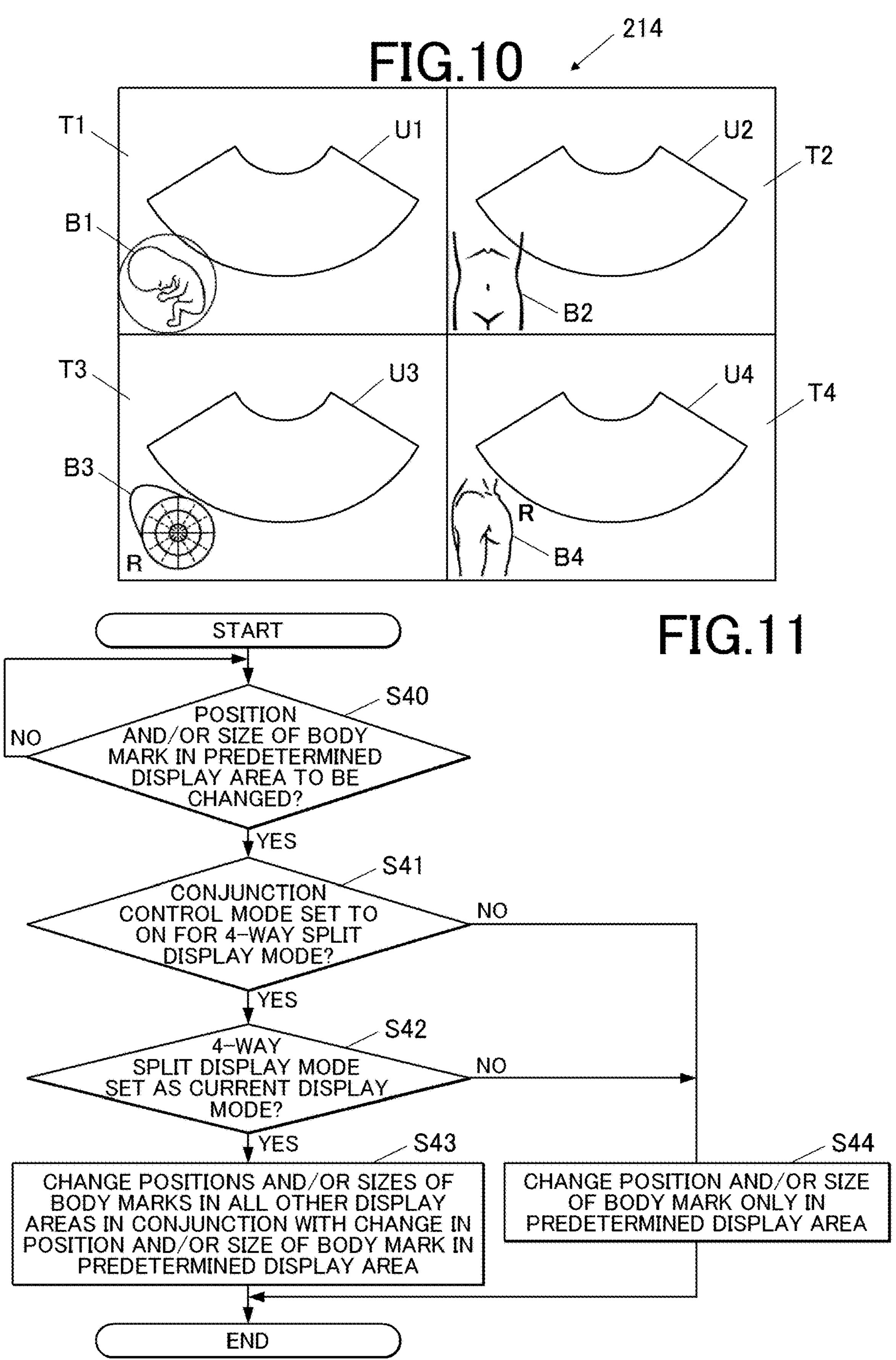
FIG.10
214
T1
U1
B1
U2
T2
B2
T3
U3
B3
R
U4
T4
R
B4
FIG.11
START
S40
POSITION AND/OR SIZE OF BODY MARK IN PREDETERMINED DISPLAY AREA TO BE CHANGED?
NO
YES
S41
CONJUNCTION CONTROL MODE SET TO ON FOR 4-WAY SPLIT DISPLAY MODE?
NO
YES
S42
4-WAY SPLIT DISPLAY MODE SET AS CURRENT DISPLAY MODE?
NO
YES
S43
CHANGE POSITIONS AND/OR SIZES OF BODY MARKS IN ALL OTHER DISPLAY AREAS IN CONJUNCTION WITH CHANGE IN POSITION AND/OR SIZE OF BODY MARK IN PREDETERMINED DISPLAY AREA
S44
CHANGE POSITION AND/OR SIZE OF BODY MARK ONLY IN PREDETERMINED DISPLAY AREA
END

ULTRASOUND DIAGNOSTIC APPARATUS, ULTRASOUND DIAGNOSTIC METHOD, AND RECORDING MEDIUM

BACKGROUND OF THE INVENTION

Technical Field

The present invention relates to an ultrasound diagnostic apparatus, an ultrasound diagnostic method, and a recording medium.

Description of Related Art

An ultrasound diagnostic apparatus irradiates an examination part such as a heart, a breast, or a fetus with ultrasound waves, and uses the reflected ultrasound waves to create an image of the inside of the examination part. The ultrasound image data of the examination part imaged by the ultrasound diagnostic apparatus is displayed on a screen of a display device. At this time, a symbol image called a body mark for visually specifying the examination part of the ultrasound image is displayed on the screen of the display device together with the ultrasound image.

The ultrasound diagnostic apparatus is provided with a split display mode in which the screen of the display device is divided into a plurality of display areas and an ultrasound image is displayed in each of the divided display areas. In the split display mode, for example, when a single examination part is imaged with different positions, directions, and/or angles, a plurality of ultrasound images are displayed in the respective divided display areas. In each display area in which the ultrasound image is displayed, a body mark for specifying the examination part of each ultrasound image is displayed.

A technology for dividing an examination screen into a plurality of areas to display ultrasound images and body marks is found in, for example, Japanese Unexamined Patent Application Publication No. 2-237555. Japanese Unexamined Patent Application Publication No. 2-237555 describes a tomographic image display apparatus that displays, in a multimode, a plurality of tomographic images in respective predetermined areas of a divided screen and a body pattern placed adjacent to each tomographic image. The body pattern is displayed in a smaller size than in a single mode.

SUMMARY OF THE INVENTION

In the split display mode, the body mark displayed in each display area may be changed to a position and/or a size that are/is easy to see. In this case, all the body marks in the divided display areas may be changed to the same position and/or the same size. However, in the related art, an operation of changing the position and/or the size has to be performed for each body mark in each display area. Therefore, there is a problem that workload of a physician or the like during an examination increases in a case where the position and/or the size of the body mark in each display area are/is changed.

In order to solve the above problem, an object of the present invention is to provide an ultrasound diagnostic apparatus, an ultrasound diagnostic method, and a recording medium capable of reducing workload of a user during an examination when the position and/or the size of a body mark are/is changed in a split display mode.

To achieve at least one of the abovementioned objects, an ultrasound diagnostic apparatus reflecting one aspect of the present invention comprises: a generator that irradiates a subject with an ultrasound wave to generate ultrasound image data based on a reflected wave of the ultrasound wave reflected off the subject; and a hardware processor that displays an ultrasound image based on the ultrasound image data on a screen of a display part, wherein, in a display mode in which the screen is divided into a plurality of display areas, the hardware processor: displays an ultrasound image of a predetermined examination part and identification information for specifying the examination part of the ultrasound image in each of the plurality of display areas; and, in response to a change made in a position and/or a size of the identification information in one display area among the plurality of display areas, executes conjunction control of changing the position and/or the size of the identification information in another display area in conjunction with the change.

To achieve at least one of the abovementioned objects, an ultrasound diagnostic method reflecting another aspect of the present invention comprises: irradiating a subject with an ultrasound wave to generate ultrasound image data based on a reflected wave of the ultrasound wave reflected off the subject; and displaying an ultrasound image based on the ultrasound image data on a screen of a display, wherein, in a display mode in which the screen is divided into a plurality of display areas, the displaying includes: displaying an ultrasound image of a predetermined examination part and identification information for specifying the examination part of the ultrasound image in each of the plurality of display areas; and, in response to a change made in a position and/or a size of the identification information in one display area among the plurality of display areas, executing conjunction control of changing the position and/or the size of the identification information in another display area in conjunction with the change.

To achieve at least one of the abovementioned objects, a recording medium reflecting yet another aspect of the present invention stores a computer-readable program, the program causing the computer to: irradiate a subject with an ultrasound wave to generate ultrasound image data based on a reflected wave of the ultrasound wave reflected off the subject; and display an ultrasound image based on the ultrasound image data on a screen of a display, wherein, in a display mode in which the screen is divided into a plurality of display areas, the program causes the computer to: display an ultrasound image of a predetermined examination part and identification information for specifying the examination part of the ultrasound image in each of the plurality of display areas; and, in response to a change made in a position and/or a size of the identification information in one display area among the plurality of display areas, execute conjunction control of changing the position and/or the size of the identification information in another display area in conjunction with the change.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein:

FIG. 4 is a flowchart illustrating an operation of the ultrasound diagnostic apparatus during an examination according to the present embodiment;

FIG. 10 is a diagram illustrating another example of ultrasound images and body marks displayed on the screen of the display part in the four-way split display mode according to the present embodiment; and FIG. 11 is a flowchart illustrating an operation of the ultrasound diagnostic apparatus when a conjunction control mode according to a modification example is applied to a specific split display mode.

DETAILED DESCRIPTION

Hereinafter, one or more embodiments of the present invention will be described with reference to the drawings. However, the scope of the invention is not limited to the disclosed embodiments.

[Exemplary Configuration of Ultrasound Diagnostic System 1]

Figure 1:
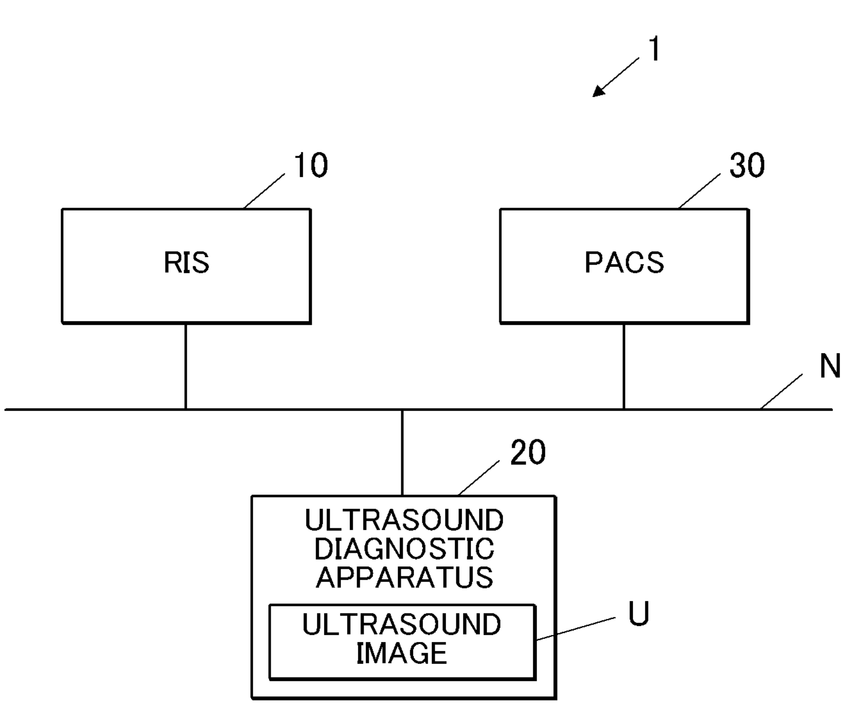
FIG. 1 is a diagram illustrating a schematic configuration of an ultrasound diagnostic system according to the present embodiment.

First, an ultrasound diagnostic system 1 according to the present embodiment will be described. FIG. 1 is a diagram illustrating a schematic configuration of the ultrasound diagnostic system 1 according to the present embodiment. As illustrated in FIG. 1, the ultrasound diagnostic system 1 includes a RIS 10, an ultrasound diagnostic apparatus 20, and a PACS 30. RIS is an abbreviation for Radiological Information System.

PACS is a medical image management system and an abbreviation for Picture Archiving and Communication System. The RIS 10, the ultrasound diagnostic apparatus 20 and the PACS 30 are communicably connected to each other via a network N such as a LAN, a WAN, or the Internet. LAN is an abbreviation for Local Area Network. WAN is an abbreviation for Wide Area Network.

The RIS 10 performs information management such as a medical examination reservation, a report of a diagnostic result, and performance management in the ultrasound diagnostic system 1. The RIS 10 transmits order information generated by an electronic medical record system (not shown) or the like to the ultrasound diagnostic apparatus 20.

The ultrasound diagnostic apparatus 20 generates an ultrasound image U corresponding to a state of an internal tissue of the living body of a patient (hereinafter, referred to as a subject) in accordance with the order information received from the RIS 10. The ultrasound diagnostic apparatus 20 generates ultrasound image data based on a received reflected ultrasound wave and displays the internal state of the subject as an ultrasound image U based on the generated ultrasound image data. The ultrasound diagnostic apparatus 20 generates supplementary information on the generated ultrasound image data based on the order information. The ultrasound diagnostic apparatus 20 generates an image file in accordance with the DICOM standard by adding the supplementary information to the ultrasound image data, and transmits the generated image file to PACS 30. DICOM is an abbreviation for Digital Imaging and Communication in Medicine.

The PACS 30 stores and manages, based on the supplementary information and the like included in the image file, the image file and a moving image file generated by the ultrasound diagnostic apparatus 20. The PACS 30 retrieves an image file or the like by using a patient ID, an examination ID or the like specified in accordance with an operation instruction of a physician or the like as a retrieval key. The PACS 30 outputs the retrieved image file or the like to a display part 214 of the ultrasound diagnostic apparatus 20, a viewer of a client information terminal (not shown), or the like.

[Exemplary Configuration of Ultrasound Diagnostic Apparatus 20]

Figure 2:
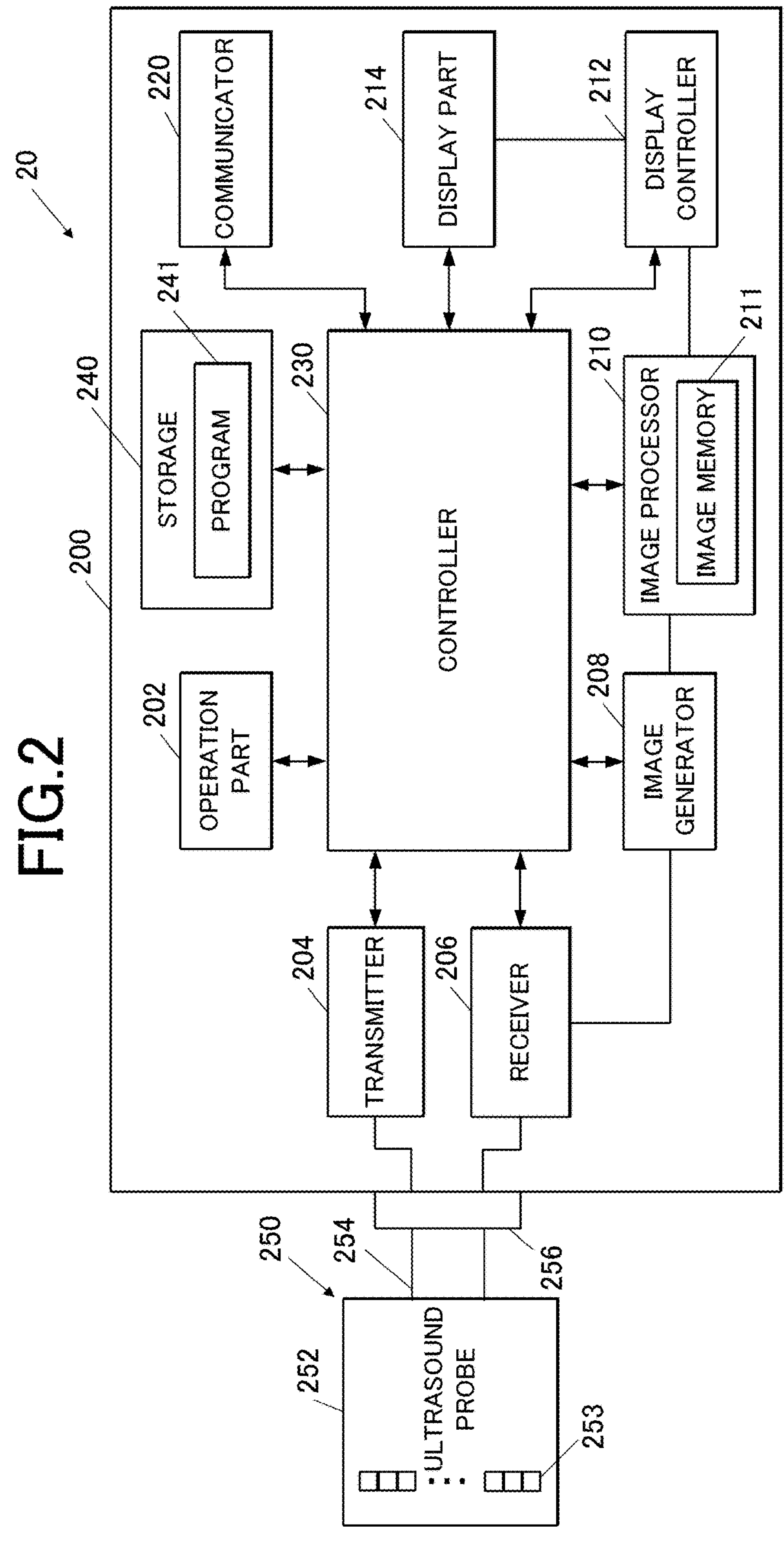
FIG. 2 is a block diagram illustrating a configuration of an ultrasound diagnostic apparatus according to the present embodiment.

Next, the ultrasound diagnostic apparatus 20 according to the present embodiment will be described. FIG. 2 is a block diagram illustrating a configuration of the ultrasound diagnostic apparatus 20 according to the present embodiment. The ultrasound diagnostic apparatus 20 is used by a user such as a physician or a technician in a medical facility such as a hospital, or the like. As illustrated in FIG. 2, the ultrasound diagnostic apparatus 20 includes an ultrasound diagnostic apparatus body 200 and an ultrasound probe 250 connected to the ultrasound diagnostic apparatus body 200.

The ultrasound diagnostic apparatus body 200 includes an operation part 202, a transmitter 204, a receiver 206, an image generator 208, and an image processor 210. The ultrasound diagnostic apparatus body 200 further includes a display controller 212, a display part 214, a communicator 220, a controller (hardware processor) 230, and a storage section 240.

The operation part 202 receives input instructions by various user operations, converts the received input instructions into electrical signals, and outputs the electrical signals to the controller 230. For example, the operation part 202 receives an input of a command for executing an installer, a parameter related to display of an ultrasound image U, and the like. The operation part 202 includes, for example, a mouse, a keyboard, a trackball, a switch, and/or a button. The operation part 202 may be, for example, a touch screen integrally combined with a display or may be a user interface such as a microphone that receives voice input. Specifically, the operation part 202 receives setting of ON/OFF of a conjunction control mode, setting of a display mode such as a two-way split display mode and a four-way split display mode, and the like.

The transmitter 204 supplies a driving signal, which is an electrical signal, to the ultrasound probe 250 under control of the controller 230. The transmitter 204 includes, for example, a clock generation circuit, a delay circuit, and a pulse generation circuit. The clock generation circuit generates a clock signal for determining the transmission timing and transmission frequency of the driving signal. The delay circuit sets a delay time for each path provided in each transducer 253 described below, and delays transmission of the driving signal by the set delay time. The delay circuit focuses a transmission beam constituted by an ultrasound wave. The pulse generation circuit generates a pulse signal as the driving signal at a predetermined cycle. The transmitter 204 drives, for example, a consecutive portion of a plurality of transducers 253 to generate a ultrasound wave. The transmitter 204 performs scanning by shifting the transducers 253 to be driven in the azimuth direction each time an ultrasound wave is generated.

Under control of the controller 230, the receiver 206 receives a reception signal, which is an electrical signal, from the ultrasound probe 250. The receiver 206 includes, for example, an amplifier, an A/D conversion circuit, and a phasing addition circuit. The amplifier amplifies the reception signal by a preset amplification factor for each path provided in each transducer 253. The A/D conversion circuit performs analog/digital conversion on the amplified reception signal. The phasing addition circuit provides a delay time to the A/D converted reception signal for each path provided in each transducer 253 to adjust the time phase, and adds the reception signals. The phasing addition circuit generates sound ray data (sound ray signal) by phasing addition. Note that the receiver 206 may include an amplifier for amplifying the reception signal.

The image generator 208 performs envelope detection processing, logarithmic compression, and the like on the sound ray data supplied from the receiver 206 under control of the controller 230. The image generator 208 further adjusts the dynamic range and gain of the sound ray data and converts the brightness thereof to generate B-mode image data. The B-mode image data represents the intensity of a reception signal by luminance and is tomographic image information about a tissue of the subject. Image data generated by the image generator 208 is not limited to image data of the B-mode. Examples of the other scan modes (image modes) include an A-mode, an M-mode, and a scan mode using the Doppler method. The Doppler method includes, for example, a color Doppler mode and a PWD. B-mode is an abbreviation for Brightness mode. A-mode is an abbreviation for Amplitude mode. M-mode is an abbreviation for Motion mode. PWD is an abbreviation for Pulsed Wave Doppler.

The image processor 210 performs image processing on the B-mode image data output from the image generator 208 under control of the controller 230. The image processor 210 performs the image processing on the B-mode image data in accordance with various image parameters being set. The image processor 210 includes an image memory 211 constituted by a semiconductor memory such as a DRAM. DRAM is an abbreviation for Dynamic Random Access Memory. The image processor 210 stores the image processed B-mode image data in the image memory 211 in units of frames under control of the controller 230. In the present embodiment, image data in units of frames may be referred to as ultrasound image data or frame image data. Under control of the controller 230, the image processor 210 sequentially outputs the image data generated as described above to the display controller 212.

The display controller 212 generates an image signal for display by performing coordinate transformation or the like on the received ultrasound image data under control of the controller 230. The display controller 212 outputs the generated image signal for display to the display part 214.

The display part 214 displays a still image or a moving image corresponding to the image signal for display output from the display controller 212 on a screen under control of the controller 230. The display part 214 is, for example, a display such as an LCD or an organic EL display. LCD is an abbreviation for Liquid Crystal Display. EL is an abbreviation for Electronic Luminescence. In the present embodiment, the display part 214 divides the screen into a plurality of display areas according to the set display mode, and displays an ultrasound image U or the like of an examination part in each display area. Examples of the display mode include a two-way split display mode and a four-way split display mode.

The communicator 220 includes, for example, a communication module including an NIC, a LAN adapter, a receiver and a transmitter. NIC is an abbreviation for Network Interface Card. The communicator 220 communicates various data, information, and the like with, for example, the RIS 10, the PACS 30, and other external devices connected via the network N.

The controller 230 includes a processor such as a CPU and a memory such as a RAM. The CPU reads various programs 241 stored in the storage section 240, develops the programs in the RAM, and executes various processes in cooperation with the programs. The CPU may be constituted by a single processor or a plurality of processors.

The controller 230 causes an ultrasound image U based on the generated ultrasound image data to be displayed on the screen of the display part 214. In a display mode in which the screen is divided into a plurality of display areas, the controller 230 displays the ultrasound image U of a predetermined examination part and a body mark for specifying the examination part of the ultrasound image U for each of the plurality of display areas. When the conjunction control mode is set to ON, in conjunction with a change in at least one of the position and size of a body mark in one display area, the controller 230 executes conjunction control of changing a body mark in another display area. Specifically, when the controller 230 acquires a change instruction to change at least one of the position and size of a body mark in one display area among the plurality of display areas, the controller 230 changes at least one of the position and size of a body mark in another display area in conjunction with the change based on the change instruction.

The ultrasound diagnostic apparatus 20 may include a computer and function as a generator that irradiates a subject with an ultrasound wave to generate ultrasound image data based on an ultrasound wave reflected off the subject by executing a program 241 or the like. Further, the ultrasound diagnostic apparatus 20 may function as a controller that displays an ultrasound image U based on generated ultrasound image data on a screen of a display part 214. The conjunction control mode described above may be executed as a function of the controller.

The storage section 240 includes a suitable storage module including, for example, an HDD, an SSD, a ROM, and a RAM. The storage section 240 stores, for example, a system program, an application program, and various types of data received by the communicator 220. The storage section 240 stores the programs 241 for executing a display mode, a conjunction control mode, processing related to an ultrasound examination, and the like.

As illustrated in FIG. 2, the ultrasound probe 250 includes a head section 252, a cable 254, and a connector 256. The head section 252 is a portion to be pressed against the subject. The head section 252 includes a plurality of transducers 253 formed of piezoelectric elements. Each of the transducers 253 transmits an ultrasound wave to the subject based on a driving signal transmitted from the ultrasound diagnostic apparatus body 200 and receives an ultrasound wave reflected off the subject. The plurality of transducers 253 may be arranged in, for example, a one-dimensional array in the scanning direction or a two-dimensional array (matrix). The number of transducers 253 can be suitably set. In the present embodiment, an electronic scanning probe with a linear scanning method is used as the ultrasound probe 250, and ultrasound waves are scanned by the linear scanning method. In addition to the linear scanning method, other scanning methods such as a convex scanning method and a sector scanning method may be employed.

The cable 254 has one end electrically connected to the head section 252 and the other end electrically connected to the connector 256. The connector 256 is attached to the other end of the cable 254 and is connected to the ultrasound diagnostic apparatus body 200. Note that the communication between the ultrasound diagnostic apparatus body 200 and the ultrasound probe 250 is not limited to wired communication using the cable 254. A communication method between the ultrasound diagnostic apparatus body 200 and the ultrasound probe 250 may be wireless communication using UWB or the like. UWB is an abbreviation for Ultra Wide Band.

[Exemplary Configuration of Body Mark B]

Figure 3:
FIG. 3 is a diagram illustrating body marks for specifying examination parts of respective ultrasound images according to the present embodiment.
Figure 5:
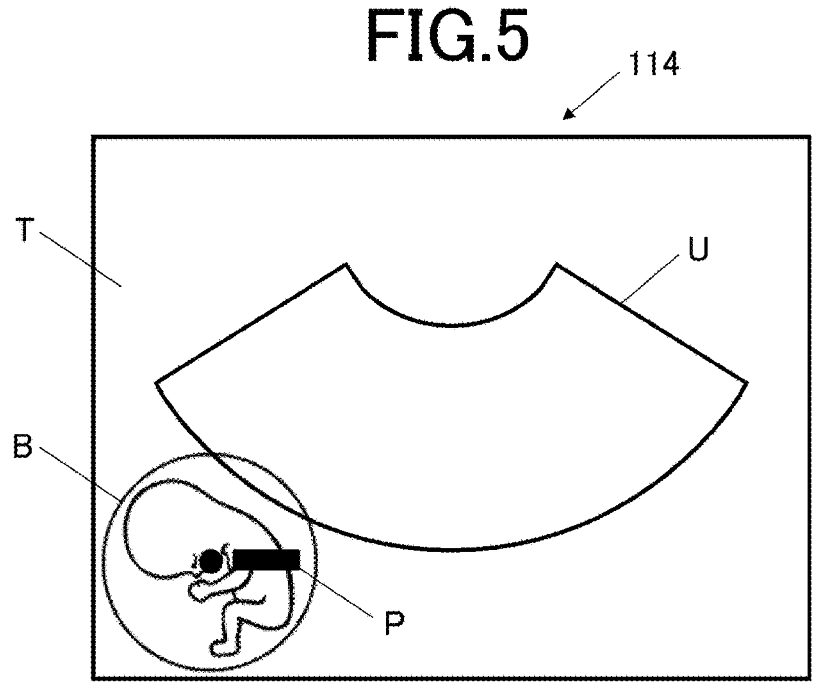
FIG. 5 is a diagram illustrating an ultrasound image and a body mark displayed on a screen of a display part according to the present embodiment.

Next, the body mark B according to the present embodiment will be described. FIG. 3 illustrates body marks B for specifying examination parts of respective ultrasound images U according to the present embodiment. Each of the body marks B is a mark for visually specifying an examination part, such as a fetus, an abdomen, a right breast, a left breast, and a right shoulder. The type of body marks B shown in FIG. 3 is an example. Each of the body marks B is superimposed on an ultrasound image U or displayed in a peripheral portion of an ultrasound image U so that an examination part of the ultrasound image U displayed on the screen of the display part 214 can be specified. As illustrated in FIG. 5, a probe mark P indicating the position, direction, and/or angle of the ultrasound probe 250 when the ultrasound probe 250 is pressed against an examination part of a subject is superimposed on a body mark B. The body mark B for specifying an examination part of an ultrasound image U and the probe mark P may be stored in the storage section 240 as a list in association with a body mark ID or the like, for example.

Note that although the body mark B is used as identification information for identifying an examination part in the present embodiment, this is not limited thereto. Any form may be adopted as long as a user such as a physician or a technician can recognize which examination part is imaged in an ultrasound image U. For example, the identification information may be a character, a symbol, or another figure (mark) for specifying an examination part. The identification information may be a combination of at least two or more of a figure, a character, and a symbol.

[Exemplary Operation of Ultrasound Diagnostic Apparatus 20]

Next, an exemplary operation of the ultrasound diagnostic apparatus 20 that executes an ultrasound diagnostic method according to the present embodiment will be described. FIG. 4 is a flowchart illustrating the operation of the ultrasound diagnostic apparatus 20 during an examination according to the embodiment. Each step illustrated in FIG. 4 is implemented when a program 241 in the storage section 240 is executed by the controller 230 that includes a processor. FIG. 5 illustrates an ultrasound image U and a body mark B displayed on the screen of the display part 214. In the drawings used in the present embodiment, ultrasound images U are illustrated in a simplified manner for descriptive purpose.

The controller 230 executes patient information input process (step S1). To be specific, the controller 230 acquires order information transmitted from the RIS 10, and acquires personal information of a patient input via the operation part 202.

The controller 230 acquires setting information on the split display mode and setting information on the conjunction control mode (step S2). The split display mode and the conjunction control mode can be set, for example, by a user input via the operation part 202 on the screen of the display part 214. In the split display mode, for example, a normal display mode, a two-way split display mode, a four-way split display mode, or the like can be selected. The split display mode may include a mode in which the screen is divided into more than four display areas. The normal display mode is a single-screen display mode. The two-way split display mode is a display mode in which the screen is divided into two (first division number) display areas. The four-way split display mode is a display mode in which the screen is divided into four (second division number) display areas. In the conjunction control mode, it is possible to select whether or not to set the conjunction control mode.

The controller 230 starts scanning operation (step S3). Specifically, the controller 230 controls the transmitter 204 and the receiver 206 to transmit and receive ultrasound waves. The image generator 208 and the image processor 210 generate ultrasound image data based on the received ultrasound waves. The controller 230 stores the generated ultrasound image data in the image memory 211 for each frame, and causes an ultrasound image U based on the ultrasound image data to be displayed on the screen of the display part 214. Step S3 corresponds to a generating step.

The controller 230 executes a body mark input process (step S4). Specifically, the controller 230 displays a body mark list in a predetermined display area of the screen of the display part 214. The controller 230 acquires identification information related to a body mark B selected from the displayed body mark list by an input operation via the operation part 202. The body mark B selected here is a body mark corresponding to an examination part to be scanned. Specifically, as illustrated in FIG. 5, when the normal mode is selected as the display mode, the body mark B of a fetus is displayed as the examination part at the lower left of the display area T of the display part 214. In this case, a probe mark P representing the position, direction, and/or angle of the ultrasound probe 250 relative to the examination part may be superimposed on the body mark B. The body mark B and the probe mark P can be moved to arbitrary positions by an input operation via the operation part 202. In the present embodiment, the display position of the body mark B is set to, for example, the lower left of each display area T by default, but may be set to another position. The default setting may be arbitrarily changed via the operation part 202. Step S4 corresponds to a display controlling step.

The controller 230 determines whether settings of various parameters have been changed (step S5). Examples of the parameters include a gamma characteristic, a gain, and a dynamic range.

If it is determined that the setting of a parameter has been changed, the controller 230 proceeds the process to step S13. The controller 230 changes the setting of the parameter in accordance with an input operation via the operation part 202 (step S13). When step S13 is completed, the controller 230 returns the process to step S5, and checks whether the setting of another parameter has been changed.

On the other hand, if the controller 230 determines that the setting of a parameter has not been changed, the controller 230 proceeds the process to step S6. The controller 230 determines whether a freeze operation has been performed (step S6). Specifically, the controller 230 determines whether an operation of switching the ultrasound image U displayed as a moving image on the display part 214 to a still image has been performed by the user. The freeze operation may be performed by, for example, touching a freeze button of the operation part 202 when the ultrasonic image U is displayed as a moving image.

If it is determined that the freeze operation has been performed, the controller 230 executes image freeze control (step S7). The image freeze control is control for fixedly displaying, as a still image, the ultrasound image U being displayed on the display part 214 when a freeze operation is received. Specifically, as shown in FIG. 5, when the normal mode is set as the display mode, the ultrasound image U of the fetus is fixedly displayed at the center of the screen. In this case, the controller 230 combines the image data of the body mark B with the image data of the ultrasound image U to be fixedly displayed and displays the body mark B and ultrasound image U obtained by the combining process. The body mark B is displayed in a smaller size than the ultrasound image U. In the present embodiment, while the ultrasound image U is fixedly displayed on the screen in the image freeze control, the scanning operation may be performed in parallel. In addition, for example, in a case where the input operation of the body mark B is forgotten in step S4, the body mark B for specifying the examination part may be input after the image freeze control is completed.

On the other hand, if it is determined that the freeze operation has not been performed, the controller 230 returns the process to step S5 and checks whether the setting of another parameter has been changed. Step S7 corresponds to a display controlling step.

The controller 230 determines whether an image saving operation has been performed (step S8). Specifically, the controller 230 determines whether the operation part 202 has received an operation to store the image data of the ultrasound image U after the combining process in the storage section 240. If it is determined in step S8 that the image saving operation has not been performed, the controller 230 proceeds the process to step S11.

On the other hand, if the controller 230 determines that the image saving operation has been performed, the controller 230 creates an image file based on the ultrasound image data combined with the body mark B (step S9). Specifically, the controller 230 reads the combined ultrasound image data corresponding to the fixedly displayed ultrasound image U from the image memory 211 and converts the read ultrasound image data into image data for storage. The image file conversion method is, for example, bitmap image, JPEG, or the like. Next, the controller 230 adds supplementary information to the converted image data and generates an image file composed of DICOM image data. Examples of the supplementary information include patient information, examination information, series information, and image identification information.

The controller 230 stores the created image file in the storage section 240 (step S10). When the saving of the image file is completed, the controller 230 determines whether to end the scanning operation (step S11). Specifically, the controller 230 determines whether an end operation of ending one examination has been received via the operation part 202. Note that whether the end operation has been received may be determined by whether a predetermined examination end operation has been performed, or whether other patient information has been read. If the controller 230 determines to end the scanning operation, the controller 230 ends the series of examination processes. On the other hand, if the controller 230 determines not to end the scanning operation, the controller 230 proceeds the process to step S12.

When the scanning operation is not to be ended, the controller 230 performs freeze release control for switching the display on the display part 214 from fixed display to moving image display (step S12). When the freeze release control is completed, the controller 230 returns the process to step S4, scans another examination part, and repeatedly executes the input process of a body mark B for specifying the examination part, and subsequent processes. When a split display mode is selected, the ultrasound image U of another examination part or the like is displayed in a display area different from the display area in which the ultrasound image U fixed by the image freeze control or the like is displayed. In this way, a series of processes such as scanning of an examination part is executed.

(In Case of Changing Position of Body Mark B)

Figure 6:
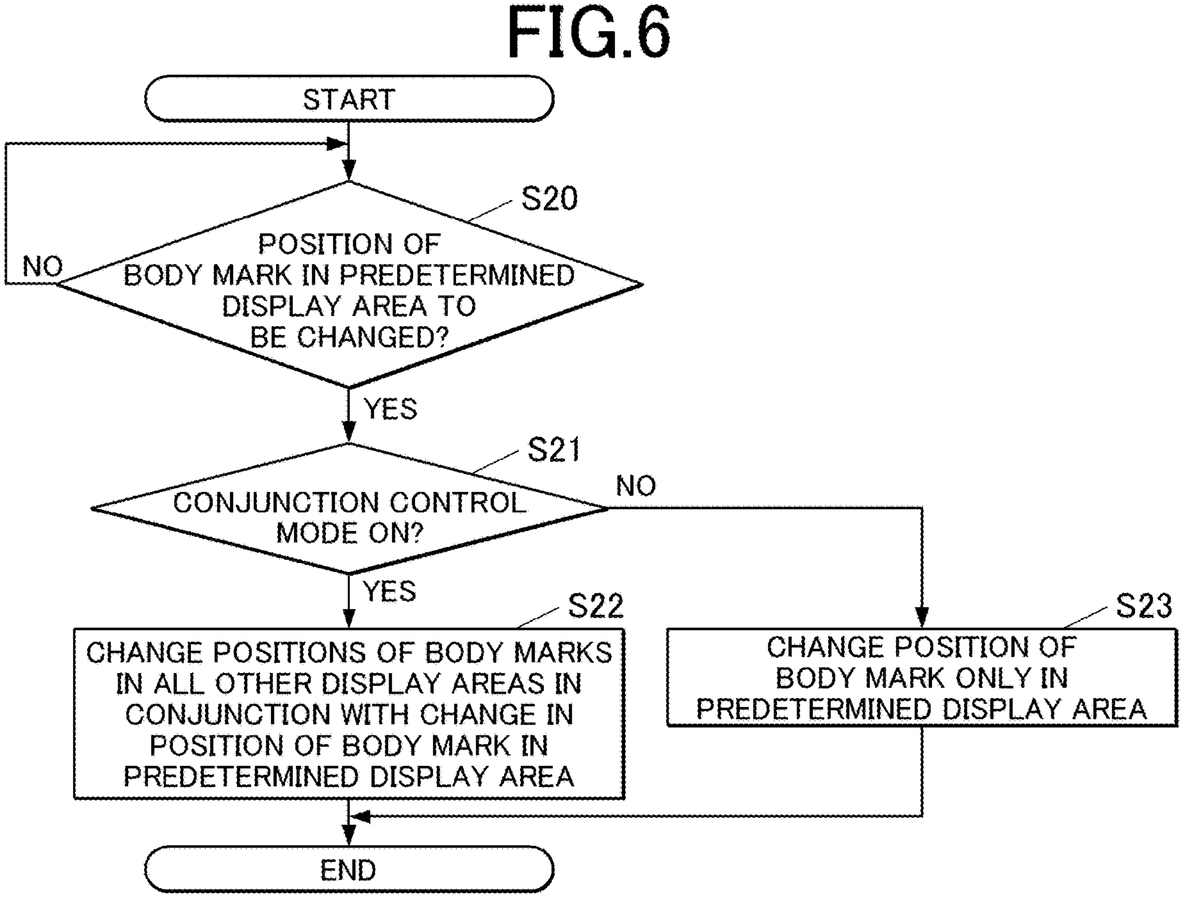
FIG. 6 is a flowchart illustrating an operation of the ultrasound diagnostic apparatus when the position of a body mark is changed in a four-way split display mode according to the present embodiment.
Figure 7A:
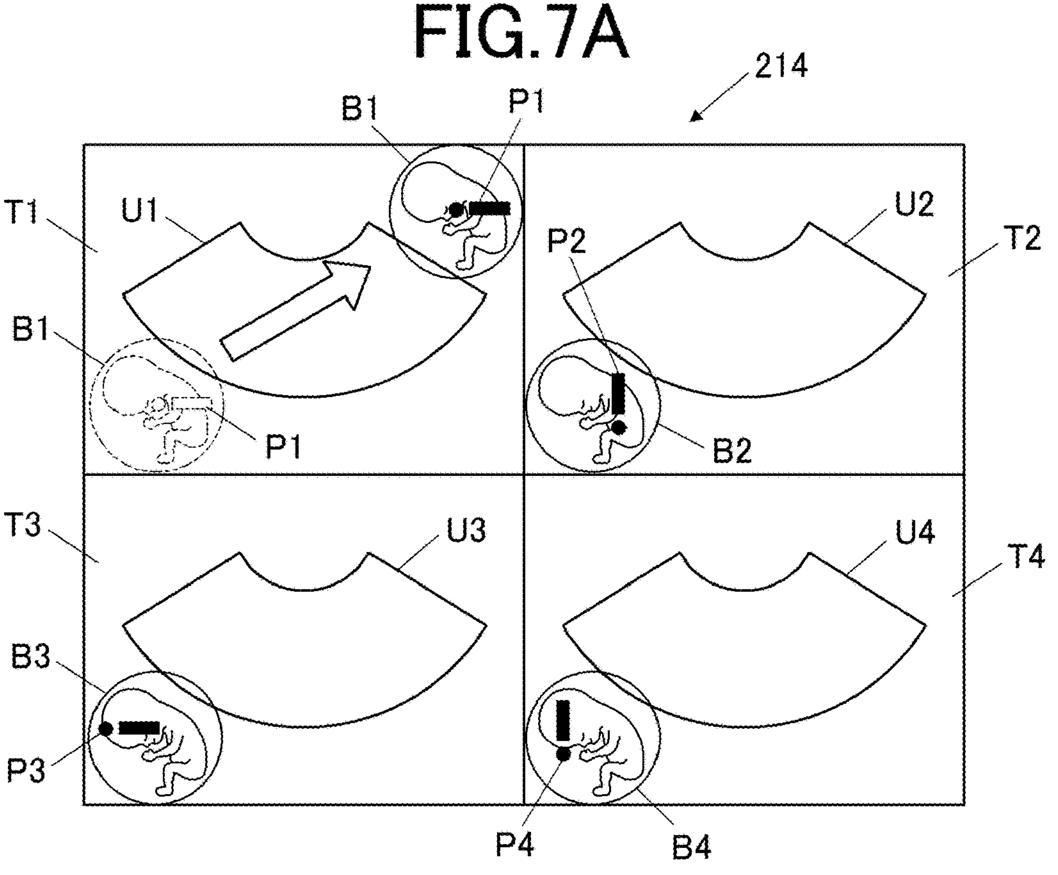
FIG. 7A is an explanatory diagram of a case where the position of a body mark in the first display area is changed in the four-way split display mode according to the present embodiment.
Figure 7B:
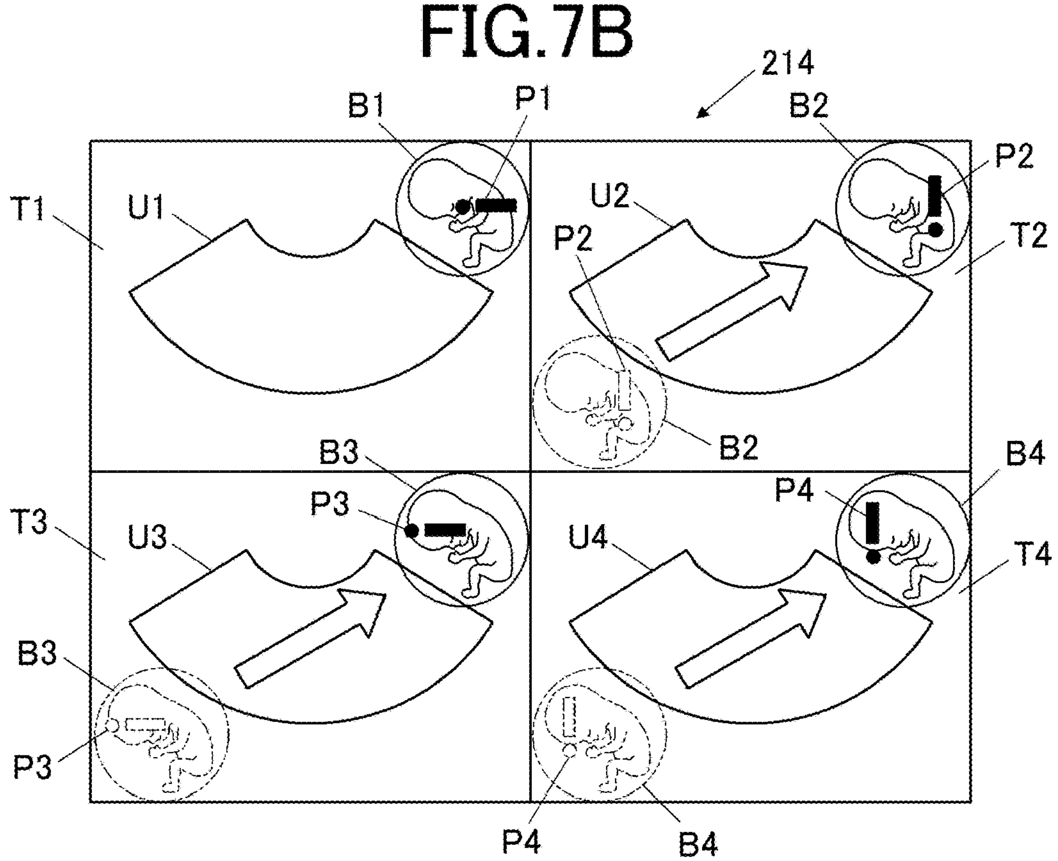
FIG. 7B is an explanatory diagram of a case where the positions of body marks in display areas other than the first display area are changed in conjunction with the change in the first display area when a conjunction control mode is ON in the four-way split display mode according to the present embodiment.

Next, an operation of the ultrasound diagnostic apparatus 20 will be described when the four-way split display mode is selected as the split display mode. FIG. 6 is a flowchart illustrating the operation of the ultrasound diagnostic apparatus 20 when the position of the body mark B is changed in the four-way split display mode according to the present embodiment; FIG. 7A is an explanatory diagram of a case where the position of the body mark B1 in the first display area T1 is changed in the four-way split display mode according to the present embodiment. FIG. 7B is an explanatory diagram of a case where the positions of the body marks B2, B3, and B4 in display areas other than the first display area T1 are changed in conjunction with the change of the body mark B1 when the conjunction control mode is ON in the four-way split display mode according to the present embodiment.

First, the four-way split display mode will be described with reference to FIG. 7A. In the four-way split display mode, the screen is split into four display areas, and an ultrasound image U and a body mark B are displayed in each of the display areas. In each display area T, an ultrasound image U of each examination part generated by executing the steps in FIG. 4 and a body mark B for specifying the examination part are displayed. In the present embodiment, the upper left area of the screen is called a first display area T1, the upper right area a second display area T2, the lower left area a third display area T3, and the lower right area a fourth display area T4.

In the center of the first display area T1, an ultrasound image U1 representing a cross-sectional image of the abdomen of a fetus as an examination part is displayed. On the lower left side of the first display area T1, a body mark B1 for specifying a fetus which is the examination part of the ultrasound image U1 is displayed. In the body mark B1, a probe mark P1 representing the ultrasound probe 250 adjusted to a position, a direction, and an angle for measuring the antero-posterior trunk diameter (APTD) is superimposed and displayed on the ultrasound image U1.

In the center of the second display area T2, an ultrasound image U2 representing a cross-sectional image of the abdomen of the fetus as an examination part is displayed. On the lower left side of the second display area T2, a body mark B2 for specifying a fetus which is the examination part of the ultrasound image B2 is displayed. In the body mark B2, a probe mark P2 representing the ultrasound probe 250 adjusted to a position, a direction, and an angle for measuring the transverse trunk diameter (TTD) is superimposed and displayed on the ultrasound image U2.

In the center of the third display area T3, an ultrasound image U3 representing a cross-sectional image of the head of the fetus as an examination part is displayed. On the lower left side of the third display area T3, a body mark B3 for specifying a fetus which is the examination part of the ultrasound image U3 is displayed. In the body mark B3, a probe mark P3 representing the ultrasound probe 250 adjusted to a position, a direction, and an angle for measuring the biparietal diameter (BPD) is superimposed and displayed on the ultrasound image U3.

In the center of the fourth display area T4, an ultrasound image U4 representing a cross-sectional image of the head of the fetus as an examination part is displayed. On the lower left side of the fourth display area T4, a body mark B4 for specifying a fetus which is the examination part of the ultrasound image U4 is displayed. In the body mark B4, a probe mark P4 representing the ultrasound probe 250 adjusted to a position, a direction, and an angle for measuring the frontal occipital diameter (FOD) is superimposed and displayed on the ultrasound image U4.

Next, the flowchart in FIG. 6 will be described. Note that steps shown in FIG. 6 may be executed, for example, immediately after the body mark input process in step S4 shown in FIG. 4 or after the start of the scanning operation in step S3 shown in FIG. 4. Furthermore, the steps shown in FIG. 6 may be executed immediately after determination that the freeze operation has not been performed in step S6 shown in FIG. 4 or immediately after the image freeze release control in step S12 shown in FIG. 4.

The controller 230 determines whether a change instruction to change the position of the body mark B in a predetermined display area T has been acquired (step S20). For example, when receiving a change instruction to change the position of the body mark B in the predetermined display area T from the user, the operation part 202 outputs the received change instruction to the controller 230.

If it is determined that a change instruction to change the position of the body mark B in the predetermined display area T has been acquired, the controller 230 proceeds the process to step S21. For example, as illustrated in FIG. 7A, the change instruction is an instruction to move the body mark B1 in the first display area T1 from a lower left position to an upper right position in the first display area T1. On the other hand, if it is determined that a change instruction to move the body mark B in the predetermined display area T has not been acquired, the controller 230 returns the process to step S20 and checks whether another change instruction has been received.

The controller 230 determines whether the conjunction control mode is set to ON (step S21). If the controller 230 determines that the conjunction control mode is set to ON, the controller 230 proceeds the process to step S22. The conjunction control mode may be set at the timing of step S2 shown in FIG. 4 or at another timing.

When the conjunction control mode is set to ON, in conjunction with the change of the position of the body mark B in the predetermined display area T, the controller 230 changes the positions of the body marks B in all the other display areas T (step S22). The controller 230 moves the body marks B in all the other display areas T in the same movement direction and by the same movement distance as the body mark B in the predetermined display area T.

To be specific, as shown in FIG. 7A, the controller 230 moves the body mark B1 in the first display area T1 from a lower left position to an upper right position in the first display area T1 based on the acquired change instruction. Subsequently, as shown in FIG. 7B, the controller 230 moves the body mark B2 in the second display area T2, the body mark B3 in the third display area T3, and the body mark B4 in the fourth display area T4 in conjunction with the body mark B1 in the first display area T1. To be specific, the controller 230 moves the body mark B2 in the second display area T2 from a lower left position to an upper right position in the second display area T2. The controller 230 moves the body mark B3 in the third display area T3 from a lower left position to an upper right position in the third display area T3. The controller 230 moves the body mark B4 in the fourth display area T4 from a lower left position to an upper right position in the fourth display area T4.

In FIGS. 7A and 7B, after the body mark B in the predetermined display area T is moved, all the body marks B in the other display areas T are moved consecutively, but the present invention is not limited thereto. For example, all the body marks B in the other display areas T may be moved at the same time or substantially the same time as the movement of the body mark B in the predetermined display area T. Thus, in the conjunction control mode, by moving the body mark B in one display area T, the body marks B in the other remaining display areas T can be moved in conjunction. That is, according to the present embodiment, all the body marks B can be moved by one operation.

On the other hand, if it is determined that the conjunction control mode is not set to ON, the controller 230 proceeds the process to step S23. If it is determined that the conjunction control mode is not set to ON, the controller 230 moves only the body mark B in the predetermined display area T based on the acquired change instruction (step S23). To be specific, as shown in FIG. 7A, the controller 230 moves the body mark T1 from a lower left position to an upper right position in the first display area B1, based on the acquired change instruction. When the conjunction control mode is not set, the controller 230 moves only the body mark B1 for which the change instruction has been received, and does not move the body marks B2, B3, and B4.

(In Case of Changing Size of Body Mark B)

Figure 8:
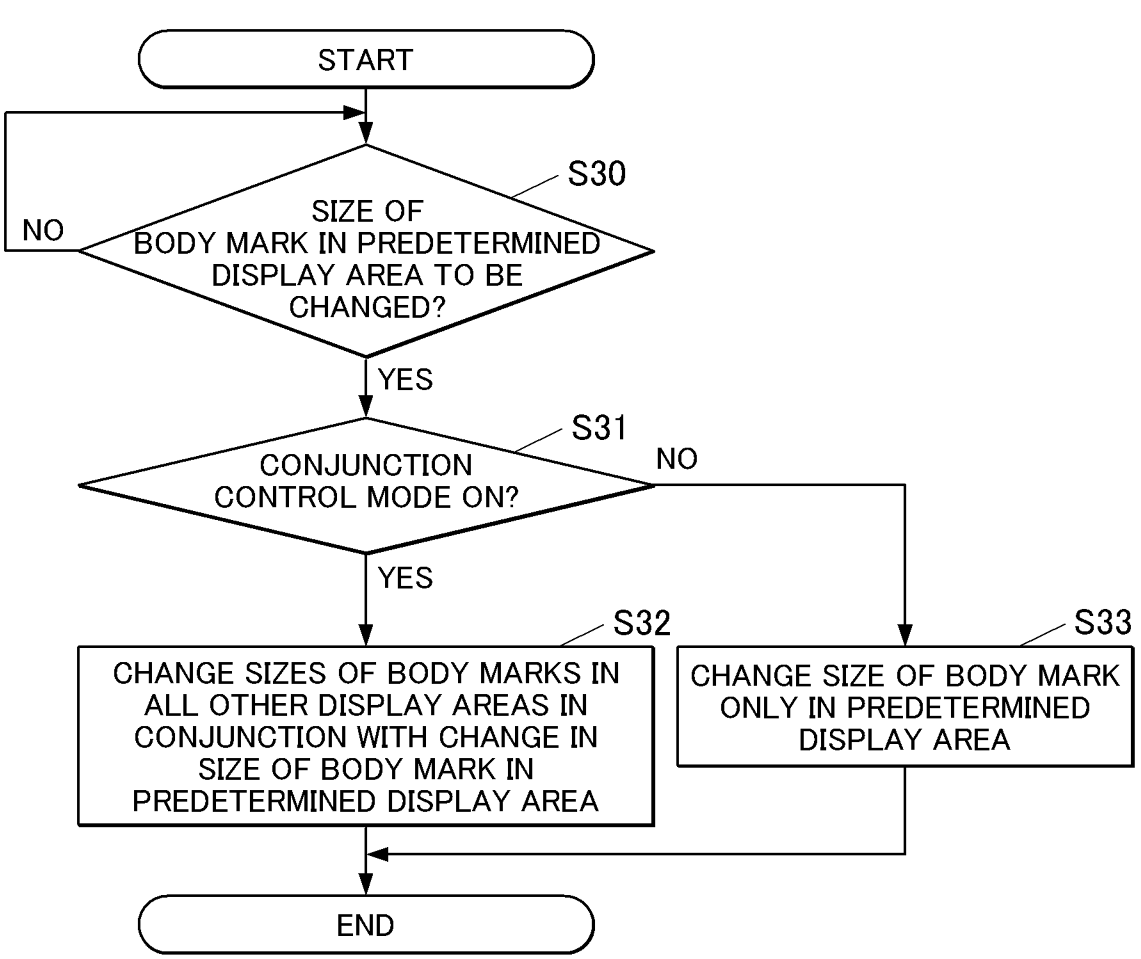
FIG. 8 is a flowchart illustrating an operation of the ultrasound diagnostic apparatus when the size of a body mark is changed in the four-way split display mode according to the present embodiment.
Figure 9A:
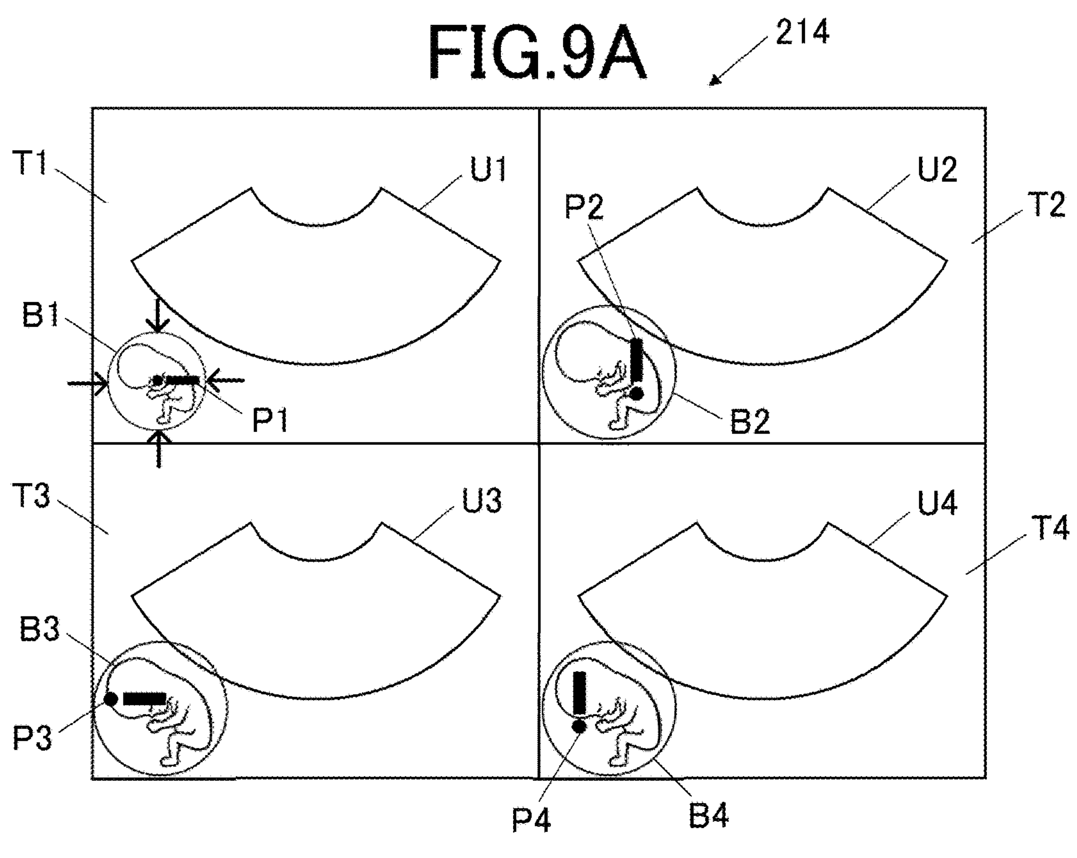
FIG. 9A is an explanatory diagram of a case where the size of a body mark in the first display area is changed in the four-way split display mode according to the present embodiment.
Figure 9B:
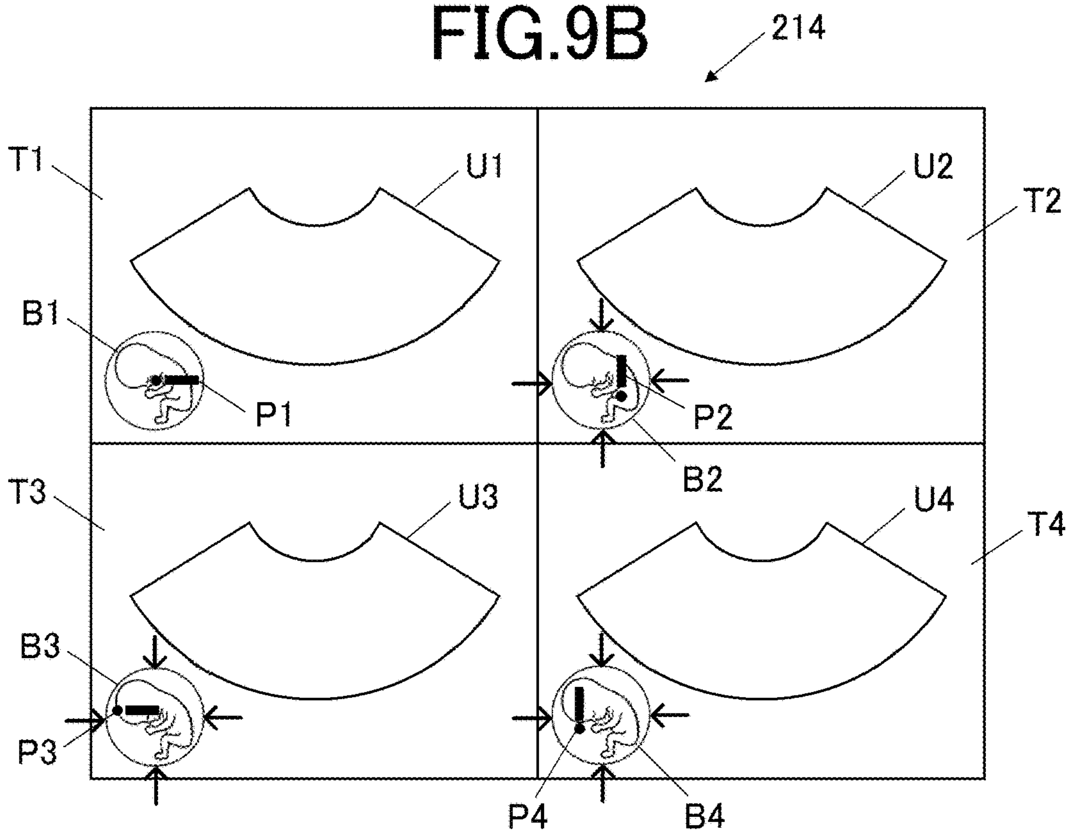
FIG. 9B is an explanatory diagram of a case where the sizes of body marks in display areas other than the first display area are changed in conjunction with the change in the first display area when the conjunction control mode is ON in the four-way split display mode according to the present embodiment.

The above-described conjunction control mode is also applicable to a case where the size of a body mark B is changed. FIG. 8 is a flowchart illustrating an operation of the ultrasound diagnostic apparatus 20 when the size of a body mark B is changed in the four-way split display mode according to the present embodiment; FIG. 9A is an explanatory diagram of a case where the size of a body mark B1 in the first display area T1 is changed in the four-way split display mode according to the present embodiment. FIG. 9B is an explanatory diagram of a case where the sizes of body marks B2, B3, and B4 in display areas other than the first display area T1 are changed in conjunction with the change of the body mark B1 when the conjunction control mode is set to ON in the four-way split display mode according to the present embodiment.

The controller 230 determines whether a change instruction to change the size of the body mark B in a predetermined display area T has been acquired (step S30). For example, when receiving a change instruction to change the size of the body mark B in the predetermined display area T from the user, the operation part 202 outputs the received change instruction to the controller 230.

If it is determined that a change instruction to change the size of the body mark B in the predetermined display area T has been acquired, the controller 230 proceeds the process to step S31. For example, as illustrated in FIG. 9A, the change instruction is an instruction to reduce the size of the body mark B1 in the first display area T1. On the other hand, if it is determined that a change instruction to change the size of the body mark B in the predetermined display area T has not been acquired, the controller 230 returns the process to step S30 and checks whether another change instruction has been received.

The controller 230 determines whether the conjunction control mode is set to ON (step S31). If the controller 230 determines that the conjunction control mode is set to ON, the controller 230 proceeds the process to step S32. The conjunction control mode may be set at the timing of step S2 shown in FIG. 4 or at another timing.

When the conjunction control mode is set to ON, in conjunction with the change of the size of the body mark B in the predetermined display area T, the controller 230 changes the sizes of the body marks B in all the other display areas T (step S32). To be specific, as shown in FIG. 9A, the controller 230 reduces the size of the body mark B1 in the first display area T1 based on the acquired change instruction. Subsequently, as shown in FIG. 9B, the controller 230 reduces the sizes of the body mark B2 in the second display area T2, the body mark B3 in the third display area T3, and the body mark B4 in the fourth display area T4 in conjunction with the body mark B1 in the first display area T1.

In FIGS. 9A and 9B, after the size of the body mark B in the predetermined display area T is reduced, the sizes of all the body marks B in the other display areas T are reduced consecutively, but the present invention is not limited thereto. For example, the sizes of all the body marks B in the other display areas T may be reduced at the same time or substantially the same time as the reduction of the size of the body mark B in the predetermined display area T. Thus, according to the conjunction control mode, by changing the size of the body mark B in one display area T, the sizes of the body marks B in the other remaining display areas T can be changed in conjunction. That is, according to the present embodiment, the sizes of the body marks B in all the display areas T can be changed by one operation.

On the other hand, if it is determined that the conjunction control mode is not set to ON, the controller 230 proceeds the process to step S33. If it is determined that the conjunction control mode is not set to ON, the controller 230 changes the size of only the body mark B in the predetermined display area T based on the acquired change instruction (step S33). To be specific, as shown in FIG. 9A, the controller 230 reduces the size of the body mark B1 only in the first display area T1 based on the acquired change instruction. When the conjunction control mode is not set, the controller 230 reduces the size of only the body mark B1 for which the change instruction has been received, and does not reduce the sizes of the body marks B2, B3, and B4.

Although the case where the size of the body mark B is reduced has been described with reference to FIGS. 9A and 9B, the conjunction control mode can also be applied to a case where the size of the body mark B is enlarged. Furthermore, in the above-described embodiment, the case where the conjunction control mode is separately applied to the case of changing the position of the body mark B and the case of changing the size of the body mark B has been described, but it is not limited thereto. For example, the conjunction control mode can also be applied to a case where both of the operation of changing the position of the body mark B and the operation of changing the size of the body mark B are performed.

(In Case of Displaying Different Body Marks B)

In FIG. 7A and the like, an example in which an ultrasound image U of the same examination part and the same body mark B for specifying the examination part are displayed in each display area of the four-way split display mode has been described, but the present invention is not limited thereto. For example, ultrasound images U of different examination parts and different body marks B for specifying the examination parts may be displayed in the respective display areas of the four-way split display mode.

FIG. 10 is a diagram illustrating another example of ultrasound images U and body marks B displayed on the screen of the display part 214 in the four-way split display mode according to the present embodiment. As illustrated in FIG. 10, in the first display area T1, an ultrasound image U1 representing a cross-sectional image of a fetus is displayed, and a body mark B1 for specifying a fetus is also displayed. In the second display area T2, an ultrasound image U2 representing a cross-sectional image of an abdomen is displayed, and a body mark B2 for specifying an abdomen is also displayed. In the third display area T3, an ultrasound image U3 representing a cross-sectional image of a right breast is displayed, and a body mark B3 for specifying a right breast is displayed. In the fourth display area T4, an ultrasound image U4 representing a cross-sectional image of a right shoulder is displayed, and a body mark B4 for specifying a right shoulder is displayed. Note that although probe marks P are omitted in FIG. 10, the probe marks P may be superimposed and displayed on the body marks B similarly to FIG. 7A.

The above-described conjunction control mode can also be applied to the case where the ultrasound images U of different examination parts and the probe marks P are displayed in the respective display areas of the display part 214 as illustrated in FIG. 10. For example, when at least one of the position and size of the body mark B1 in the first display area T1 is changed, at least one of the position and size of the other body marks B2, B3, and B4 can be changed in conjunction with the change of the body mark B1.

(Body Mark Set)

In an ultrasound examination, a plurality of examination parts may be imaged in a predetermined order. For example, in an echo examination of a fetus, an ultrasound image for measuring the antero-posterior trunk diameter of the abdomen is acquired first, and an ultrasound image for measuring the transverse trunk diameter of the abdomen is acquired second. Subsequently, in the echo examination of the fetus, an ultrasound image for measuring the biparietal diameter of the head is acquired third, and an ultrasound image for measuring the frontal occipital diameter of the head is acquired fourth. In this case, it is possible to provide in advance a body mark set in which the order of the examination parts of the ultrasound images is associated with the order of the body marks B for specifying the respective examination parts. In addition, since the position or the like of the ultrasound probe 250 may be changed in the same examination part, a body mark set may be created by combining probe marks P with a body mark B. The body mark set is stored in, for example, the storage section 240. The body mark set is an example of an identification information set.

The controller 230 automatically applies the body mark B to each display area using a body mark set when the split display mode is set and an order of measuring a plurality of examination parts is determined in advance. Hereinafter, a specific description will be provided. When a freeze operation has been performed on the first examination part, the controller 230 displays an ultrasound image U1 in the first display area T1, reads a body mark B1 corresponding to the first examination part from the body mark set, and displays the body mark B1 in the first display area T1. When a freeze operation has been performed on the second examination part, the controller 230 displays an ultrasound image U2 in the second display area T2, reads a body mark B2 corresponding to the second examination part from the body mark set, and displays the body mark B2 in the second display area T2. When a freeze operation has been performed on the third examination part, the controller 230 displays an ultrasound image U3 in the third display area T3, reads a body mark B3 corresponding to the third examination part from the body mark set, and displays the body mark B3 in the third display area T3. When a freeze operation has been performed on the fourth examination part, the controller 230 displays an ultrasound image U4 in the fourth display area T4, reads a body mark B4 corresponding to the fourth examination part from the body mark set, and displays the body mark B4 in the fourth display area T4.

Modification Example

A modification example is different from the above embodiment in that the conjunction control mode is applied only to a specific split display mode. Note that differences from the above-described embodiment will be mainly described, and description of points common to the above-described embodiment will be omitted. In addition, in the description of the modification example, the same reference numerals will be given to the same parts as those in the above-described embodiment.

FIG. 11 is a flowchart illustrating an operation of the ultrasound diagnostic apparatus 20 when the conjunction control mode according to the modification example is applied to a specific split display mode. For the split display mode, the two-way split display mode and the four-way split display mode will be described as examples.

The controller 230 determines whether a change instruction to change at least one of the position and size of a body mark B in a predetermined display area T has been acquired (step S40).

If it is determined that a change instruction to change at least one of the position and size of the body mark B has been acquired, the controller 230 proceeds the process to step S41. On the other hand, if it is determined that a change instruction to change at least one of the position and size of the body mark B has not been acquired, the controller 230 returns the process to step S40 and checks whether another change instruction has been received. The controller 230 determines whether the four-way split display mode is set as the split display mode to which the conjunction control mode is applied (step S41). The setting of the conjunction control mode to ON and the setting of the display mode may be performed, for example, in step S2 in FIG. 4, or may be performed at another timing. The reasons why the conjunction control mode is applied to the four-way split display mode instead of the two-way split display mode are as follows. In the four-way split display mode, the number of divisions of the screen is larger and the size of one display area is smaller than in the two-way split display mode. Therefore, in a case where the position and/or the size of the body mark B are/is changed for each display area, detailed operations via the operation part 202 are required, and workload of the user during an examination may increase. In addition, in a case where the divided display areas are smaller, there are a fewer requests to change the position and/or the size of the body mark B for each display area. If the controller 230 determines that the four-way split display mode is set, the controller 230 proceeds the process to step S42.

The controller 230 determines whether the current setting of the display mode is the four-way split display mode (step S42). The setting of the display mode may be determined, for example, based on the setting information acquired in step S2 in FIG. 4. If the controller 230 determines that the current setting of the display mode is the four-way split display mode, the controller 230 proceeds the process to step S43.

In conjunction with a change in at least one of the position and size of the body mark B in the predetermined display area T, the controller 230 changes at least one of the position and size of the body marks B in all the other display areas T (step S43).

On the other hand, if it is determined in step S41 that the conjunction control mode is not set or if it is determined in step S42 that the display mode is other than the four-way split display mode, the controller 230 proceeds the process to step S44. The case where the display mode is other than the four-way split display mode is, for example, a case of the normal single-screen display mode, the two-way split display mode, or the like. In this case, the controller 230 changes at least one of the position and size of only the body mark B in the predetermined display area T specified based on the acquired change instruction (step S44).

In the related art, in a case where the position and/or the size of the body mark B are changed in the four-way split display mode, detailed operations are required, and there is a case where the time and effort of the user during an examination increase. In addition, in a case where the display area is small as in the four-way split display mode, there are cases where there are a few requests to change the position and size of the body mark B in each display area. According to the present modification example, the four-way split display mode can be selected as the division display mode to which the conjunction control mode is applied. Thus, by changing the position and/or the size of the body mark B in one display area, the positions and/or the sizes of the body marks B in all the remaining display areas can be changed in conjunction with the change. Thus, since all the body marks B can be collectively changed to the same position and/or the same size by one operation, the workload of the user during an examination can be reduced. Furthermore, since the conjunction control mode is not applied to the two-way split display mode, the position and/or the size of the body mark B can be freely changed for each display area in accordance with the size, direction, and/or the like of an ultrasound image U in the two-way split display mode.

Although the preferred embodiments of the present disclosure have been described in detail with reference to the accompanying drawings, the technical scope of the present disclosure is not limited to such examples. Furthermore, those to which various modification examples and improvements have been applied within the category of the technical idea described in the scope of the claims of those skilled in the art naturally belong to the technical scope of the present disclosure.

For example, when a transition is made from the two-way split display mode to the four-way split display mode, a body mark B and a probe mark P used in a display area that is active in the two-way split display mode may be taken over in the four-way split display mode. Furthermore, in a live transition of the four-way split display mode, when a body mark B is set in the transition source, it may be possible to set whether to take over the body mark B in the transition source to the transition destination. Further, even when not all the display areas are used in the four-way split display mode or the like, for example, even when only three display areas are used, the conjunction control mode according to the present embodiment can be applied. Although embodiments of the present invention have been described and illustrated in detail, the disclosed embodiments are made for purposes of illustration and example only and not limitation. The scope of the present invention should be interpreted by terms of the appended claims.

The entire disclosure of Japanese Patent Application No. 2023-200469 filed on Nov. 28, 2023, is incorporated herein by reference in its entirety.

What is claimed is:

1. An ultrasound diagnostic apparatus, comprising:

a generator that is configured to irradiate a subject with an ultrasound wave to generate ultrasound image data based on a reflected wave of the ultrasound wave reflected off the subject; and a hardware processor that displays an ultrasound image based on the ultrasound image data on a screen of a display part, wherein, in a display mode in which the screen is divided into a plurality of display areas, the hardware processor:

displays an ultrasound image of a predetermined examination part and identification information for specifying the examination part of the ultrasound image in each of the plurality of display areas;

in response to a change made by a user input in a position and/or a size of the identification information in one display area among the plurality of display areas does not execute conjunction control when a number of divisions of the screen is a first number of divisions, and, in response to a change made by a user input in a position and/or a size of the identification information in one display area among the plurality of display areas, executes conjunction control of changing the position and/or the size of the identification information in another display area in conjunction with the change when the number of divisions of the screen is a second number of divisions greater than the first number of divisions.

2. The ultrasound diagnostic apparatus according to claim 1, wherein the identification information is a body mark, a character, and/or a symbol.

3. The ultrasound diagnostic apparatus according to claim 1, wherein the first number of divisions is two, and the second number of divisions is four.

4. The ultrasound diagnostic apparatus according to claim 1, further comprising an operation part that receives a setting of whether to execute the conjunction control.

5. The ultrasound diagnostic apparatus according to claim 1, wherein the hardware processor displays the identification information that differs between the plurality of display areas.

6. The ultrasound diagnostic apparatus according to claim 1, wherein the hardware processor uses an identification information set that is a combination of the identification information for a plurality of examination parts to sequentially read the identification information from the identification information set, and displays the identification information read in the respective plurality of display areas.

7. An ultrasound diagnostic method comprising:

irradiating a subject with an ultrasound wave to generate ultrasound image data based on a reflected wave of the ultrasound wave reflected off the subject; and displaying an ultrasound image based on the ultrasound image data on a screen of a display part, wherein, in a display mode in which the screen is divided into a plurality of display areas, the displaying includes:

displaying an ultrasound image of a predetermined examination part and identification information for specifying the examination part of the ultrasound image in each of the plurality of display areas;

in response to a change made by a user input in a position and/or a size of the identification information in one display area among the plurality of display areas not executing conjunction control when a number of divisions of the screen is a first number of divisions, and, in response to a change made by a user input in a position and/or a size of the identification information in one display area among the plurality of display areas, executing conjunction control of changing the position and/or the size of the identification information in another display area in conjunction with the change when the number of divisions of the screen is a second number of divisions greater than the first number of divisions.

8. A non-transitory recording medium storing a computer-readable program, the computer-readable program when executed by a computer, being configured to cause:

a generator to irradiate a subject with an ultrasound wave to generate ultrasound image data based on a reflected wave of the ultrasound wave reflected off the subject; and display an ultrasound image based on the ultrasound image data on a screen of a display part, wherein, in a display mode in which the screen is divided into a plurality of display areas, the program causes the computer to:

display an ultrasound image of a predetermined examination part and identification information for specifying the examination part of the ultrasound image in each of the plurality of display areas;

in response to a change made by a user input in a position and/or a size of the identification information in one display area among the plurality of display areas does not execute conjunction control when a number of divisions of the screen is a first number of divisions, and, in response to a change made by a user input in a position and/or a size of the identification information in one display area among the plurality of display areas, execute conjunction control of changing the position and/or the size of the identification information in another display area in conjunction with the change when the number of divisions of the screen is a second number of divisions greater than the first number of divisions.

* * * * *